US010204865B2

(12) United States Patent
Hu et al.

(10) Patent No.: US 10,204,865 B2
(45) Date of Patent: *Feb. 12, 2019

(54) ELECTRONIC PACKAGE AND CONDUCTIVE STRUCTURE THEREOF

(71) Applicant: PHOENIX PIONEER TECHNOLOGY CO., LTD., Hsinchu County (TW)

(72) Inventors: Chu-Chin Hu, Hsinchu County (TW); Shih-Ping Hsu, Hsinchu County (TW)

(73) Assignee: PHOENIX PIONEER TECHNOLOGY CO., LTD., Hsinchu County (TW)

( * ) Notice: Subject to any disclaimer, the term of this patent is extended or adjusted under 35 U.S.C. 154(b) by 68 days.

This patent is subject to a terminal disclaimer.

(21) Appl. No.: 14/990,891

(22) Filed: Jan. 8, 2016

(65) Prior Publication Data
US 2016/0212851 A1 Jul. 21, 2016

(30) Foreign Application Priority Data

Jan. 16, 2015 (CN) .......................... 2015 1 0023069

(51) Int. Cl.
H05K 5/00 (2006.01)
H05K 1/18 (2006.01)
H01L 23/538 (2006.01)
H01L 31/00 (2006.01)
G06K 9/00 (2006.01)
H05K 7/00 (2006.01)
H01L 23/02 (2006.01)
H01L 31/054 (2014.01)
H05K 3/28 (2006.01)
H01L 31/0232 (2014.01)
A61B 5/1172 (2016.01)
(Continued)

(52) U.S. Cl.
CPC ........ *H01L 23/5389* (2013.01); *G06K 9/0004* (2013.01); *H01L 31/00* (2013.01); *H05K 1/185* (2013.01); *A61B 5/0077* (2013.01); *A61B 5/1172* (2013.01); *H01L 23/49861* (2013.01); *H01L 31/0232* (2013.01); *H01L 31/054* (2014.12); *H01L 2224/45144* (2013.01); *H01L 2224/48091* (2013.01); *H01L 2924/15311* (2013.01); *H01L 2924/16235* (2013.01); *H01L 2924/181* (2013.01); *H05K 3/284* (2013.01); *H05K 2201/10121* (2013.01); *H05K 2201/10151* (2013.01)

(58) Field of Classification Search
CPC .... H05K 1/185; H05K 2201/10; H05K 3/284; H01L 31/0232; H01L 31/054; H01L 31/02325
USPC ........................ 361/760, 761, 764, 767, 783; 257/432–434, 678, 680, E33.07
See application file for complete search history.

(56) References Cited

U.S. PATENT DOCUMENTS

2007/0164449 A1* 7/2007 Wang ...................... H01L 24/16 257/778
2008/0096321 A1* 4/2008 Lin ................... H01L 27/14618 438/113
2013/0026589 A1* 1/2013 Wu ................... H01L 27/14618 257/432

* cited by examiner

Primary Examiner — Binh Tran
(74) Attorney, Agent, or Firm — Amin, Turocy & Watson LLP

(57) ABSTRACT

An electronic package is provided, which includes: an insulator; an electronic element embedded in the insulator and having a sensing area exposed from the insulator; and a conductive structure disposed on the insulator and electrically connected to the electronic element, thereby reducing the thickness of the overall structure.

18 Claims, 10 Drawing Sheets

(51) Int. Cl.
*H01L 23/498* (2006.01)
*A61B 5/00* (2006.01)

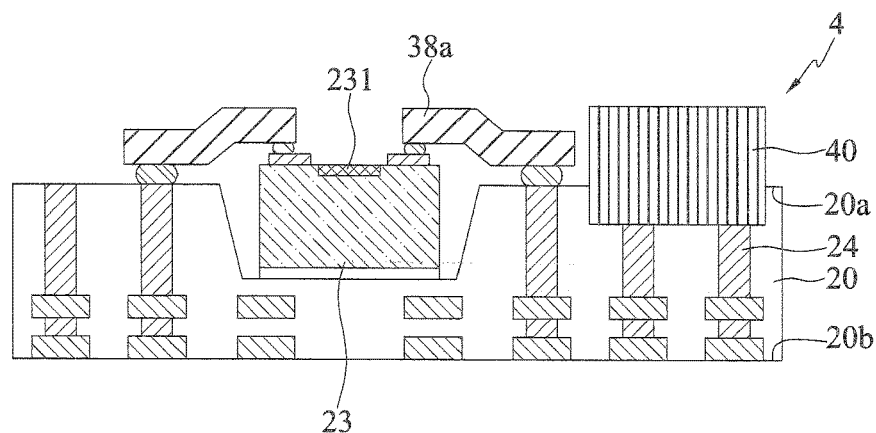
FIG.4
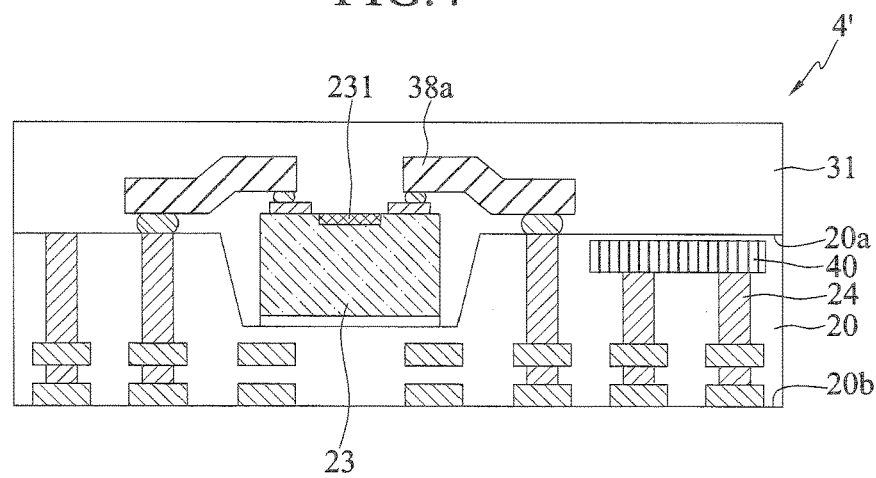
FIG.4'
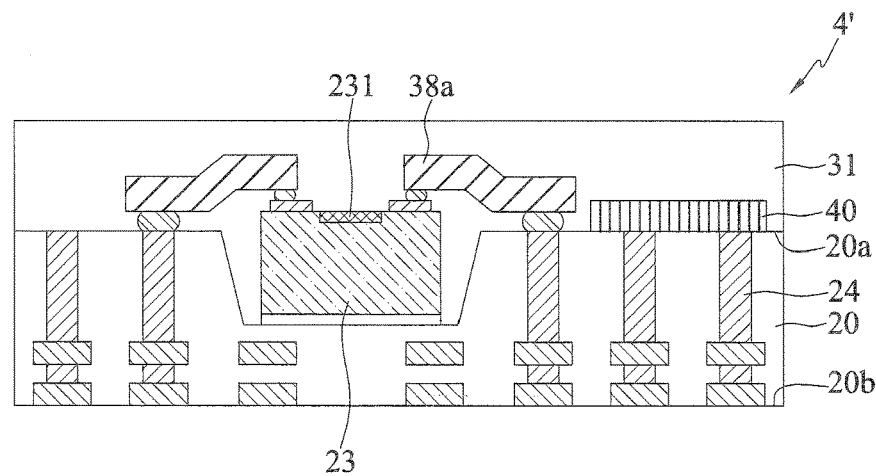
FIG.4"

ELECTRONIC PACKAGE AND CONDUCTIVE STRUCTURE THEREOF

BACKGROUND

1. Technical Field

The present disclosure relates to an electronic package, and more particularly, to a thin-type electronic package and a conductive structure thereof.

2. Description of Related Art

Along with the rapid development of electronic industries, electronic products are developed toward the trend of miniaturization and multi-function. Accordingly, various types of packages have been developed.

Generally, electronic elements of sensor elements and camera lenses are packaged to form wire-bonding or COB (Chip on Board) type package structures.

FIG. 1A is a schematic cross-sectional view of a conventional wire-bonding type package structure 1. Referring to FIG. 1A, the conventional wire-bonding type package structure 1 has a substrate 10, an electronic element 13 disposed on the substrate 10, and an encapsulant 18 formed on the substrate 10 and encapsulating the electronic element 13.

A first circuit layer 11 and a second circuit layer 12 are formed on upper and lower sides of the substrate 10, respectively, and a plurality of conductors 14 such as conductive through holes or conductive vias are formed in the substrate 10 for electrically connecting the first circuit layer 11 and the second circuit layer 12. Further, a first insulating layer 16 is formed on the upper side of the substrate 10, and portions of the first circuit layer 11 are exposed from the first insulating layer 16. A second insulating layer 17 is formed on the lower side of the substrate 10, and portions of the second circuit layer 12 are exposed from the second insulating layer 17. Furthermore, a plurality of conductive elements 15 are formed on the exposed portions of the second circuit layer 12.

The electronic element 13 is disposed on the upper side of the substrate 10 and electrically connected to the first circuit layer 11 through a plurality of gold wires 130. The electronic element 13 is a sensor element, which has a sensing area 131 formed on an upper surface thereof for fingerprint identification.

The electronic element 13 and the gold wires 130 are encapsulated by the encapsulant 18.

In the conventional wire-bonding type package structure 1, the sensing area 131 is covered by the encapsulant 18. The encapsulant 18 covering the sensing area 131 is required to have a very small thickness d with high precision so as to ensure effective sensing of the electronic element 13.

However, the gold wires 130 have a certain wire loop, and the molding process needs a sufficient height to allow the electronic element 13 to be uniformly encapsulated by the encapsulant 18. As such, the thickness of the encapsulant 18 is difficult to control and thinning of the wire-bonding type package structure 1 cannot be achieved.

FIG. 1B is a schematic cross-sectional view of a conventional COB type package structure 1'. Referring to FIG. 1B, the conventional COB type package structure 1' has a substrate 10', an electronic element 13 of a camera lens disposed on the substrate 10', a transparent element 19 disposed on the electronic element 13, and an encapsulant 18 formed on the substrate 10' and encapsulating the electronic element 13 and the transparent element 19.

The structure of the substrate 10' can be referred to the structure of FIG. 1A.

The electronic element 13 is disposed on an upper side of the substrate 10' and electrically connected to the substrate 10' through a plurality of gold wires 130. The electronic element 13 has a sensing area 131 formed on an upper surface thereof for light sensing.

The transparent element 19 is disposed on the upper surface of the electronic element 13 through a plurality of support members 190 and covers the sensing area 131 of the electronic element 13.

The encapsulant 18 is made of a non-transparent material. The encapsulant 18 is formed on the upper side of the substrate 10 and encapsulates the transparent element 19, the electronic element 13 and the gold wires 130. An upper surface of the transparent element 19 is exposed from the encapsulant 18.

In the conventional COB type package structure 1', the camera lens is required to be thinned. However, since the electronic element 13 is attached to the substrate 10' and the transparent element 19 is disposed on the electronic element 13 through the support members 190, it is not easy to thin the COB type package structure 1'.

Accordingly, through silicon via (TSV) technologies are used to overcome the above-described drawbacks. FIG. 1C is a schematic cross-sectional view of a conventional light-sensing package structure 1". Referring to FIG. 1C, the conventional light-sensing package structure 1" has a silicon substrate 10" and a transparent element 19' disposed on the silicon substrate 10".

A first circuit layer 11 and a second circuit layer 12 are formed on upper and lower sides of the silicon substrate 10", respectively, and a plurality of conductive through silicon vias 100 are formed in the silicon substrate 10" for electrically connecting the first circuit layer 11 and the second circuit layer 12. Further, a sensing area 131 is formed on the upper side of the silicon substrate 10". An insulating layer 17' is formed on the lower side of the silicon substrate 10", and portions of the second circuit layer 12 are exposed from the insulating layer 17'. Further, a plurality of conductive elements 15 are formed on the exposed portions of the second circuit layer 12.

The transparent element 19' is attached to the upper side of the silicon substrate 10" through an adhesive layer 190' and covers the sensing area 131.

However, the conductive through silicon vias 100 are difficult to fabricate and integrate and have a high fabrication cost, especially when they are applied in electronic elements of sensor elements and camera lenses.

Therefore, how to overcome the above-described drawbacks has become critical.

SUMMARY

In view of the above-described drawbacks, the present disclosure provides an electronic package, which comprises: an insulator having opposite first and second surfaces; an electronic element embedded in the first surface of the insulator and having at least a sensing area exposed from the first surface of the insulator; and a conductive structure disposed on the first surface of the insulator and electrically connected to the electronic element, wherein the sensing area is exposed from the conductive structure.

The present disclosure provides another electronic package, which comprises: an insulator having opposite first and second surfaces; an electronic element embedded in and protruding from the first surface of the insulator and having at least a sensing area exposed from the first surface of the insulator; and a conductive structure having a plurality of height levels, wherein the conductive structure is disposed on the first surface of the insulator and electrically connected to the electronic element, and the sensing area of the electronic element is exposed from the conductive structure.

In one embodiment of the above-described electronic packages, a circuit structure can be formed in the insulator, communicating with the first surface of the insulator and electrically connected to the conductive structure.

In one embodiment of the above-described electronic packages, the conductive structure can be a lead frame. The conductive structure can be electrically connected to the electronic element or another electronic element through a plurality of conductive bumps.

In one embodiment of the above-described electronic packages, the conductive structure can have a lead frame having a plurality of openings and a plurality of conductive bumps formed in the openings of the lead frame and electrically connected to the electronic element.

In one embodiment of the above-described electronic packages, the conductive structure can have a plurality of protruding contacts electrically connected to the electronic element.

In one embodiment, the above-described electronic packages can further comprise a plurality of conductive elements formed on the second surface of the insulator.

In one embodiment of the above-described electronic packages, a recessed portion can be formed on the first surface of the insulator for receiving the electronic element.

In one embodiment, the above-described electronic packages can further comprise a covering layer covering the sensing area of the electronic element.

In one embodiment of the above-described electronic packages, the conductive structure can have a step shape.

In one embodiment, the above-described electronic packages can further comprise another electronic element bonded to the insulator. The another electronic element can be an active element, a passive element or a combination thereof. In an embodiment, the another electronic element is partially disposed in the insulator and partially protrudes from the first surface of the insulator, and the another electronic element is electrically connected to a plurality of conductive posts formed in the insulator. In another embodiment, the another electronic element is completely disposed in the insulator. In a further embodiment, the another electronic element is completely disposed on the first surface of the insulator.

In one embodiment, the above-described electronic packages can further comprise a transparent element covering the sensing area of the electronic element.

In one embodiment, the above-described electronic packages can further comprise a plurality of conductive posts embedded in the insulator and electrically connected to the conductive structure.

The present disclosure further provides a conductive structure for an electronic package. The conductive structure comprises: at least one lead frame; and a plurality of conductive bumps formed on the lead frame.

In one embodiment of the above-described conductive structure, the conductive structure has a plurality of the lead frames arranged in a ring shape.

In one embodiment of the above-described conductive structure, the lead frame and the conductive bumps can be integrally formed.

In one embodiment of the above-described conductive structure, a carrier is further included, and the lead frame is disposed on the carrier.

The present disclosure further provides a conductive structure for an electronic package. The conductive structure comprises: a carrier; and at least one lead frame disposed on the carrier and having a plurality of openings.

In one embodiment of the above-described conductive structure, the conductive structure has a plurality of the lead frames, and the plurality of the lead frames are arranged in a ring shape.

In one embodiment of the above-described conductive structure, the conductive bumps are disposed in the openings when the electronic package is assembled.

By embedding the electronic element in the insulator, the present disclosure reduces the thickness of the overall electronic package.

BRIEF DESCRIPTION OF DRAWINGS

FIG. 2-5 is a top view of the conductive structures of FIGS. 2-1 to 2-4;

FIGS. 3 and 3' are schematic cross-sectional views of electronic packages according to a second embodiment of the present disclosure, wherein

FIGS. 4, 4' and 4" are schematic cross-sectional views of electronic packages according to a third embodiment of the present disclosure; and FIGS. 5 and 5' are schematic cross-sectional views of electronic packages according to a fourth embodiment of the present disclosure.

DETAILED DESCRIPTION OF PREFERRED EMBODIMENTS

The following illustrative embodiments are provided to illustrate the disclosure of the present disclosure, these and other advantages and effects can be apparent to those in the art after reading this specification.

It should be noted that all the drawings are not intended to limit the present disclosure. Various modifications and variations can be made without departing from the spirit of the present disclosure. Further, terms such as "on", "first", "second", "a," etc. are merely for illustrative purposes and should not be construed to limit the scope of the present disclosure.

FIGS. 2A to 2D are schematic cross-sectional views of electronic packages 2a to 2d according to a first embodiment of the present disclosure. The electronic packages 2a to 2d are applicable in, for example, fingerprint identifiers and image sensors. Further, FIGS. 2-1 to 2-4 are schematic cross-sectional views of conductive structures 28a to 28d of the present disclosure.

Figure 1A:
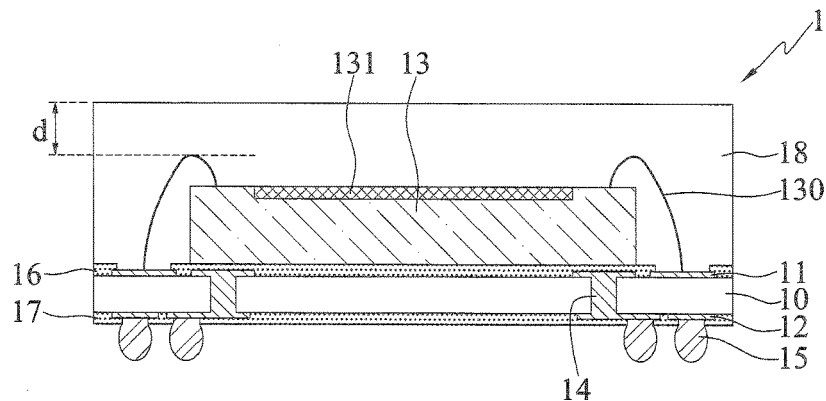
FIG. 1A is a schematic cross-sectional view of a conventional wire-bonding type package structure.
Figure 1B:
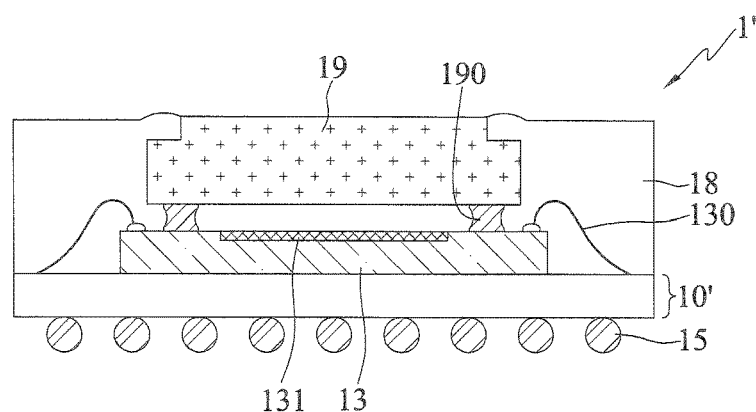
FIG. 1B is a schematic cross-sectional view of a conventional COB type package structure.
Figure 1C:
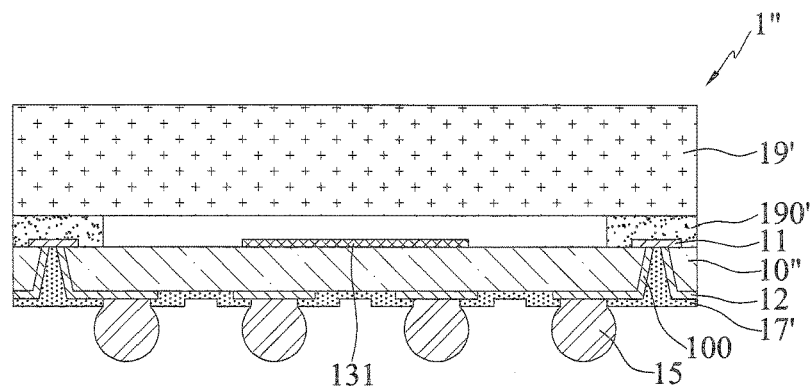
FIG. 1C is a schematic cross-sectional view of a conventional light-sensing package structure.
Figures 1, 2:
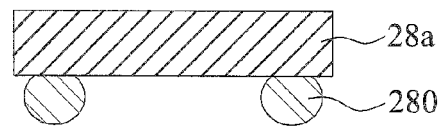
FIGS. 2-1 to 2-4 are schematic cross-sectional views showing various embodiments of the conductive structures of the present disclosure.
Figure 2:
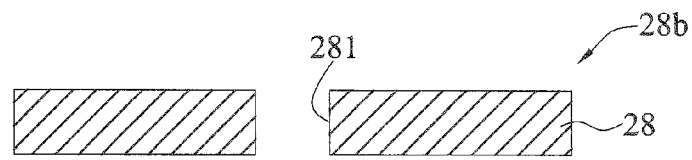
Figures 2, 3:
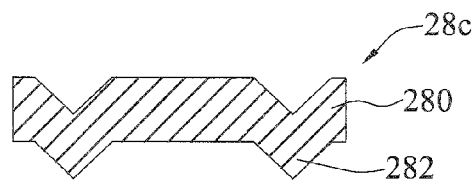
Figures 2, 3, 4:
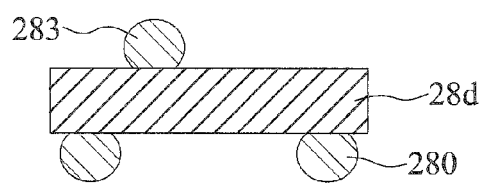
Figures 2, 3, 4, 5:
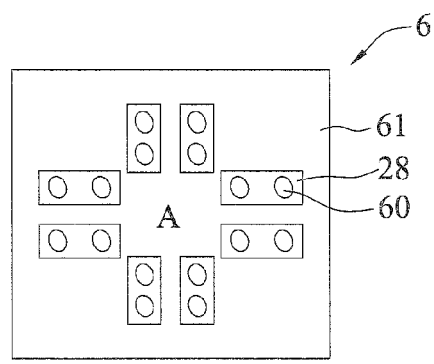
Figure 2A:
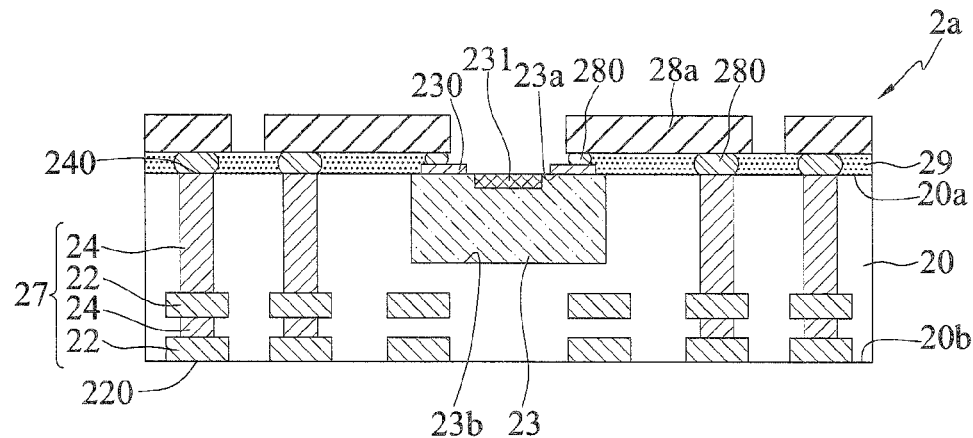
FIGS. 2A to 2D are schematic cross-sectional views of electronic packages according to a first embodiment of the present disclosure, wherein FIGS. 2A' to 2D' show another embodiment of FIGS. 2A to 2D, respectively.
Figure 2A:
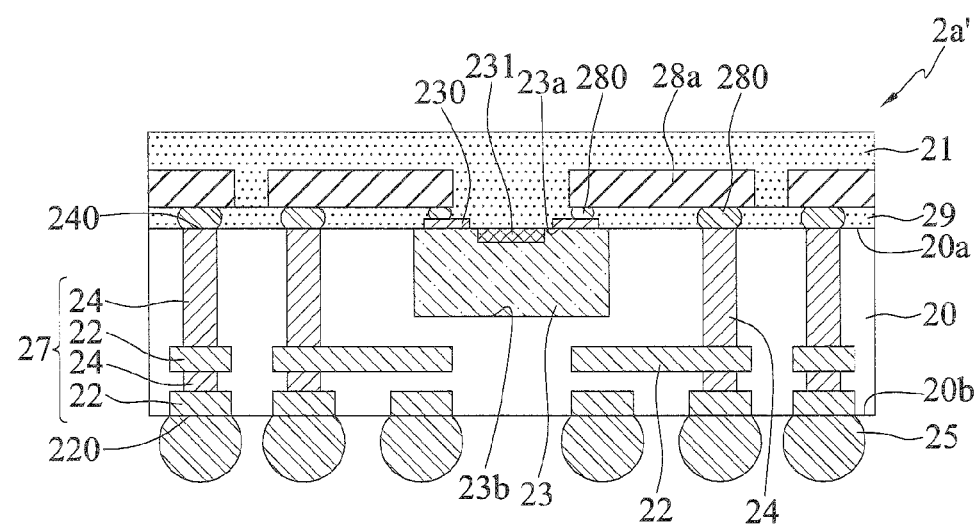

Referring to FIG. 2A, the electronic package 2a has: an insulator 20 having opposite first and second surfaces 20a, 20b; an electronic element 23 embedded in the first surface 20a of the insulator 20; a circuit structure 27 formed in the insulator 20; and a conductive structure 28a disposed on the first surface 20a of the insulator 20 and electrically connected to the electronic element 23 and the circuit structure 27.

In the present embodiment, the insulator 20 is made of a molding compound, or a dielectric material such as an epoxy resin, polyimide or other photosensitive or non-photosensitive organic resin.

The electronic element 23 is a sensor element, which has an active surface 23a with a sensing area 231 and a plurality of electrode pads 230 and an inactive surface 23b opposite to the active surface 23a. The sensing area 231 is a light sensing area or a fingerprint sensing area. The sensing area 231 and the electrode pads 230 of the electronic element 23 are exposed from the first surface 20a of the insulator 20. The active surface 23a of the electronic element 23 is flush with or slightly lower than the first surface 20a of the insulator 20.

The circuit structure 27 is formed in the insulator 20 and communicating the first surface 20a and the second surface 20b of the insulator 20.

In the present embodiment, the circuit structure 27 has a plurality of circuit layers 22 and a plurality of conductive posts 24 electrically connecting the circuit layers 22. Further, the conductive posts 24 communicate with the first surface 20a of the insulator 20 and thus end surfaces of the conductive posts 24 serve as conductive pads 240. The circuit layers 22 communicate with the second surface 20b of the insulator 20 and thus exposed surfaces of the circuit layers 22 serve as conductive pads 220. In particular, the circuit layers 22 and the conductive posts 24 are made of such as copper and formed by patterned electroplating, deposition or etching.

The conductive pads 220 of the circuit layers 22 can be flush with, or slightly higher or lower than the second surface 20b of the insulator 20. The conductive pads 240 of the conductive posts 24 can be flush with, or slightly higher or lower than the first surface 20a of the insulator 20.

Further, the circuit layers 22 are not in contact with the inactive surface 23b of the electronic element 23. That is, a portion of the insulator 20 is sandwiched between the circuit layers 22 and the inactive surface 23b of the electronic element 23.

The conductive structure 28a is as shown in FIG. 2-1. The conductive structure 28a is disposed on the first surface 20a of the insulator 20 and electrically connected to the electronic element 23 and the circuit structure 27. The sensing area 231 of the electronic element 23 is exposed from the conductive structure 28a.

In the present embodiment, the conductive structure 28a is a lead frame. The conductive structure 28a comes into contact with the electrode pads 230 and the conductive pads 240 through a plurality of conductive bumps 280 made of solder or metal adhesive. As such, the conductive structure 28a is electrically connected to the electronic element 23 and the circuit structure 27.

Further, the conductive structure 28a is formed on the first surface 20a of the insulator 20 through a bonding layer 29. The bonding layer 29 is made of an insulating material such as a dielectric material or a solder mask material. The bonding layer 29 covers a portion of the active surface 23a of the electronic element 23 and exposes the sensing area 231 of the electronic element 23.

Referring to FIG. 2A, the electronic package 2a is applicable to LGA (Land Grid Array) packages. That is, the electronic package 2a is disposed on an electronic device such as a circuit board (not shown) through the conductive pads 220 of the circuit layers 22.

Alternatively, referring to FIG. 2A', the electronic package 2a' further has a plurality of conductive elements 25 formed on the second surface 20b of the insulator 20. As such, the electronic package 2a' is applicable to BGA (Ball Grid Array) packages. In subsequent processes, the electronic package 2a' can be disposed on an electronic device such as a circuit board (not shown) through the conductive elements 25.

In the present embodiment, the conductive elements 25 are solder balls, solder bumps or copper bumps. The conductive elements 25 are formed on the conductive pads 220 of the circuit layers 22 and electrically connected to the circuit structure 27.

Further, referring to FIG. 2A', the electronic package 2a' further has a covering layer 21 formed on the conductive structure 28a and covering the sensing area 231 of the electronic element 23. The covering layer 21 can be made of such as an insulating material. In particular, the covering layer 21 can be made of a material that is the same as or different from that of the bonding layer 29. Further, the covering layer 21 and the bonding layer 29 can be formed integrally or separately (as shown in FIG. 2A').

Furthermore, referring to FIG. 2A', the conductive path constituted by the conductive structure 28a, the conductive posts 24 and the circuit layers 22 extends below the inactive surface 23b of the electronic element 23.

Other embodiments of the conductive structure are detailed as follows.

Figure 2B:
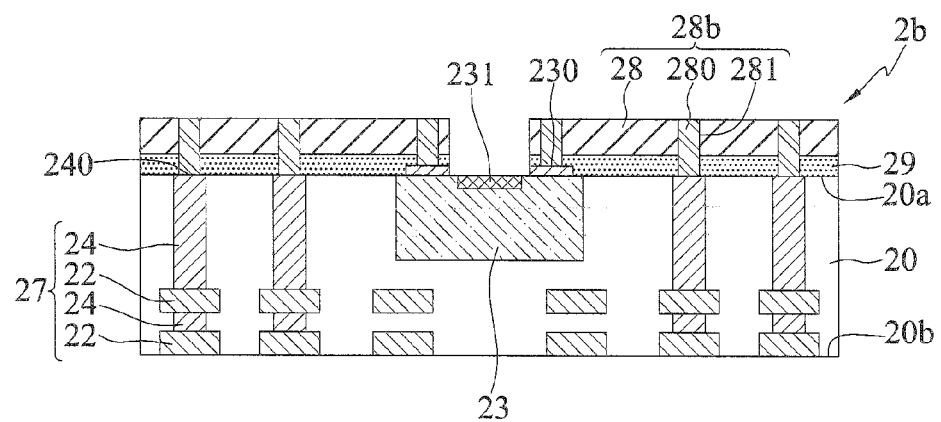
Figure 2B:
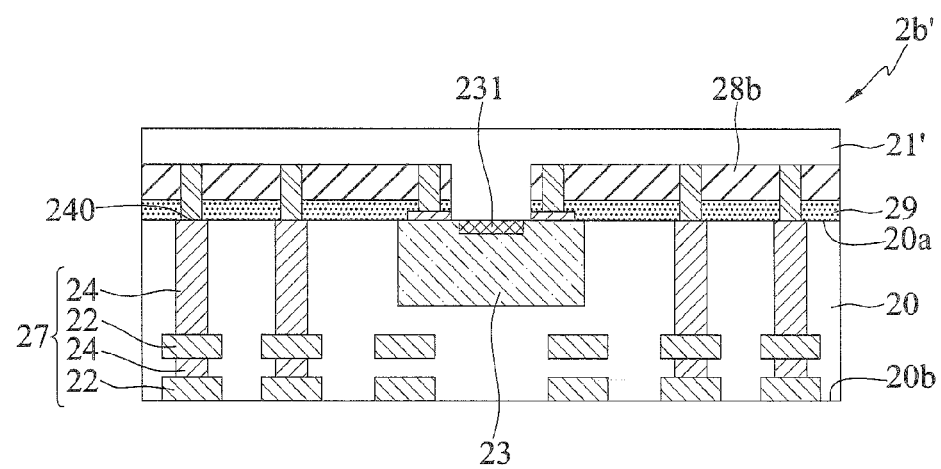

Referring to FIG. 2B and FIG. 2-2, the conductive structure 28b of the electronic package 2b has a lead frame 28 having a plurality of openings 281 and a plurality of conductive bumps 280 formed in the openings 281 and electrically connected to the electrode pads 230 and the conductive posts 24.

To fabricate the electronic package 2b, the lead frame 28 is disposed on the first surface 20a of the insulator 20 with the openings 281 corresponding in position to the electrode pads 230 and the conductive posts 24 (i.e., the conductive pads 240). Then, a conductive material made of solder or metal adhesive is filled in the openings 281 to form the conductive bumps 280.

Alternatively, referring to FIG. 2B', the electronic package 2b' further has a covering layer 21' formed on the conductive structure 28b and covering the sensing area 231 of the electronic element 23. The covering layer 21' can be made of a material that is the same as or different from that of the bonding layer 29.

Figure 2C:
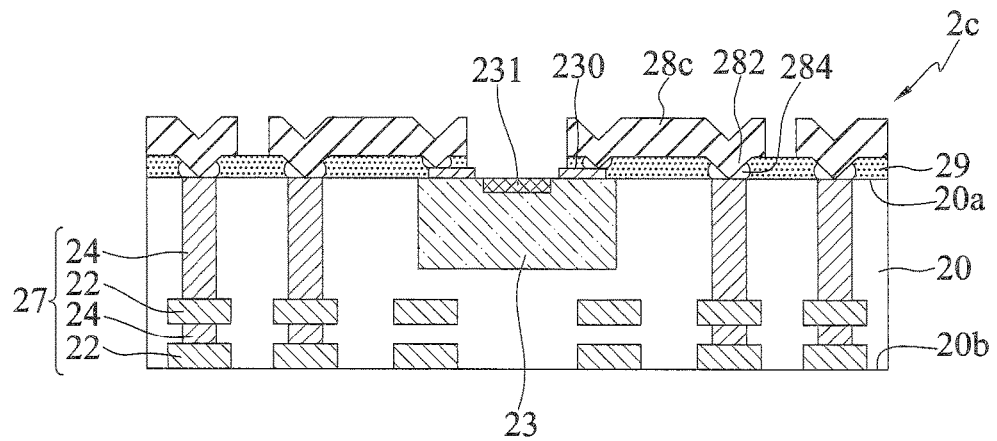
Figure 2C:
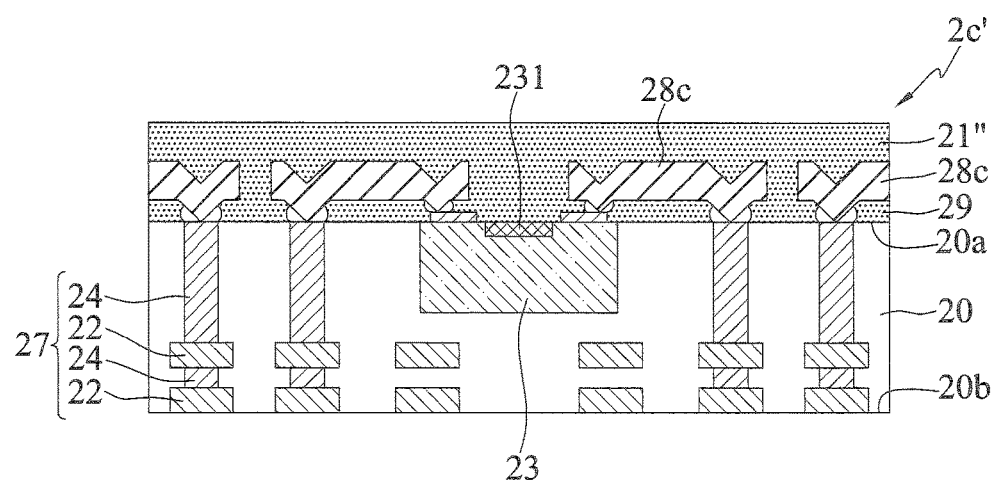

Referring to FIG. 2C and FIG. 2-3, the conductive structure 28c of the electronic package 2c has a plurality of integrally formed protruding contacts 282 serving as conductive bumps. The protruding contacts 282 are bonded and electrically connected to the electrode pads 230 and the conductive posts 24 through an adhesive material 284 such as a conductive adhesive or an insulating adhesive.

To form the protruding contacts 282, a flat lead frame is stamped from an upper side thereof so as to form the protruding contacts 282 on a lower side of the flat lead frame.

Alternatively, referring to FIG. 2C', the electronic package 2c' further has a covering layer 21" formed on the conductive structure 28c and covering the sensing area 231 of the electronic element 23. The covering layer 21' can be made of a material that is the same as or different from that of the bonding layer 29.

Referring to FIG. 2D and FIG. 2-4, in the conductive structure 28d of the electronic package 2d, a plurality of conductive bumps 280 are formed on a lower side of the conductive structure 28d and electrically connected to the electrode pads 230 and the conductive posts 24, and a plurality of conductive bumps 283 are formed on an upper side of the conductive structure 28d and electrically connected to other electronic elements 26.

In the present embodiment, the electronic elements 26 are active elements such as semiconductor chips, passive elements such as resistors, capacitors or inductors, or a combination thereof. In the present embodiment, the electronic elements 26 are passive elements.

Figure 2D:
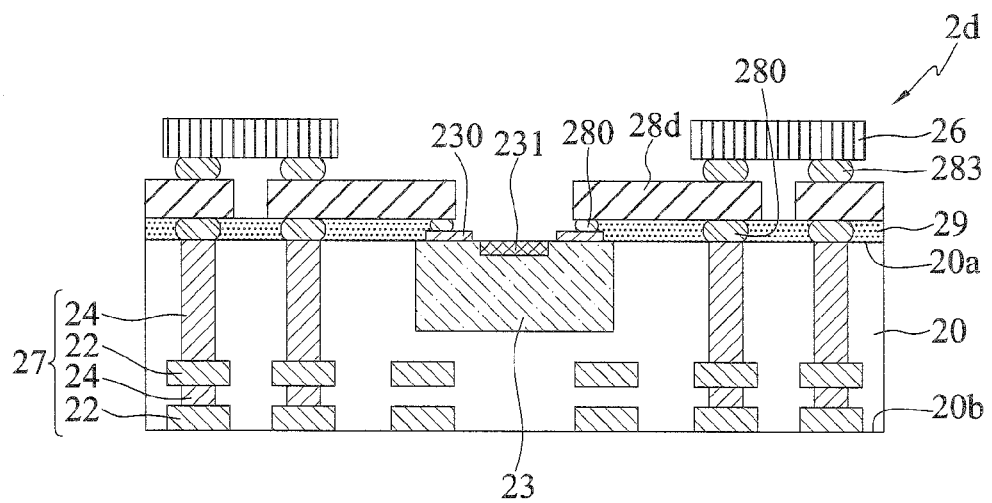
Figure 2D:
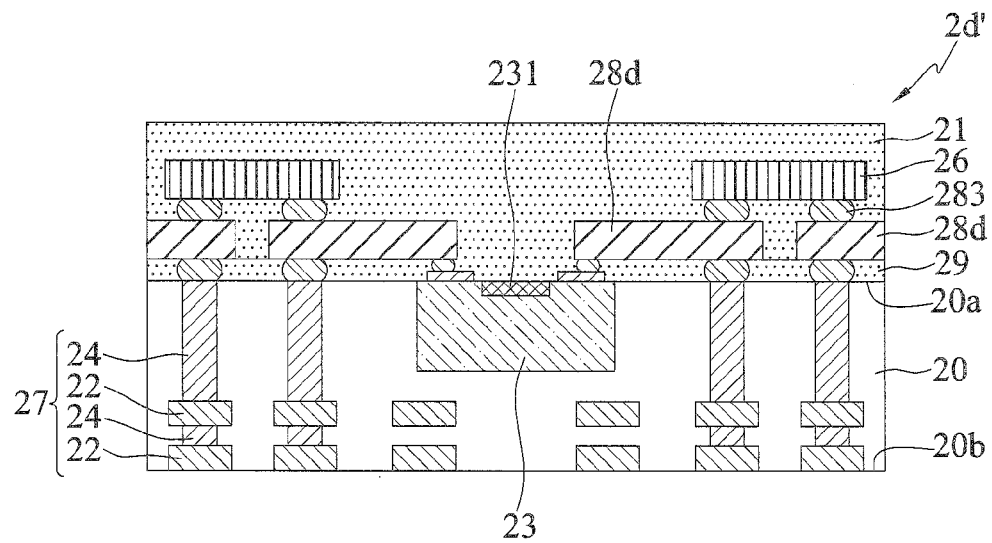

Alternatively, referring to FIG. 2D', the electronic package 2d' further has a covering layer 21 formed on the conductive structure 28d and covering the sensing area 231 and the electronic elements 26.

In the electronic packages 2a to 2d and 2a' to 2d', since the electronic element 23 is embedded in the insulator 20, the thickness of the overall structure is reduced.

Further, the conductive structures 28a to 28d are flat lead frames without any bend, thus facilitating to reduce the thickness of the overall structure. In an embodiment, the conductive structures 28a to 28d are made of pure metal or a combination of metal and an organic film.

FIGS. 3 and 3' are schematic cross-sectional views of electronic packages 3, 3' according to a second embodiment of the present disclosure. The second embodiment differs from the first embodiment in the disposing of the electronic element 23.

Referring to FIGS. 3 and 3', a recessed portion 300 is formed on the first surface 20a of the insulator 20 and the electronic element 23 is disposed in the recessed portion 300.

In the present embodiment, the inactive surface 23b of the electronic element 23 is attached to a bottom surface of the recessed portion 300 through an adhesive layer 33, and the electronic element 23 protrudes from the first surface 20a of the insulator 20. As such, the conductive structure 38a is a lead frame having a plurality of height levels. For example, the conductive structure 38a has a step shape.

Referring to FIG. 3, a covering layer 31 is formed on the first surface 20a of the insulator 20 and covering the conductive structure 38a, the conductive bumps 280 and the sensing area 231 of the electronic element 23. Further, the covering layer 31 is formed in the recessed portion 300 to fix the electronic element 23.

Alternatively, referring to FIG. 3', the conductive structure 38a is disposed on the first surface 20a of the insulator 20 through a bonding layer 39. As such, portions of the conductive bumps 280' are fixed by the bonding layer 39. The bonding layer 39 is further formed in the recessed portion 300 to fix the electronic element 23, and the sensing area 231 is exposed from the bonding layer 39. Thereafter, a covering layer 31 is formed on the bonding layer 39 to cover the conductive structure 38a, portions of the conductive bumps 280 and the sensing area 231.

The covering layer 31 can be made of a material that is the same as or different from that of the bonding layer 39. The covering layer 31 and the bonding layer 39 can be formed integrally or separately.

Figure 3:
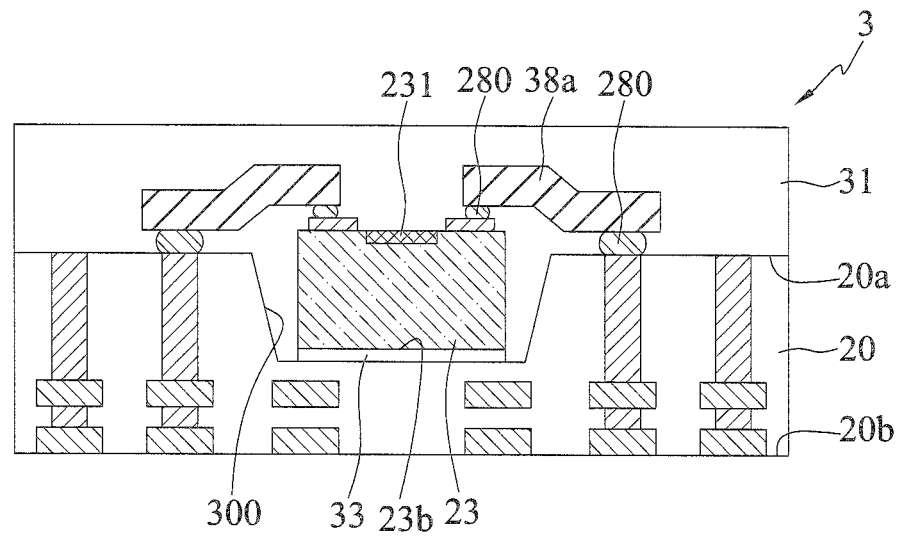
Figure 3:
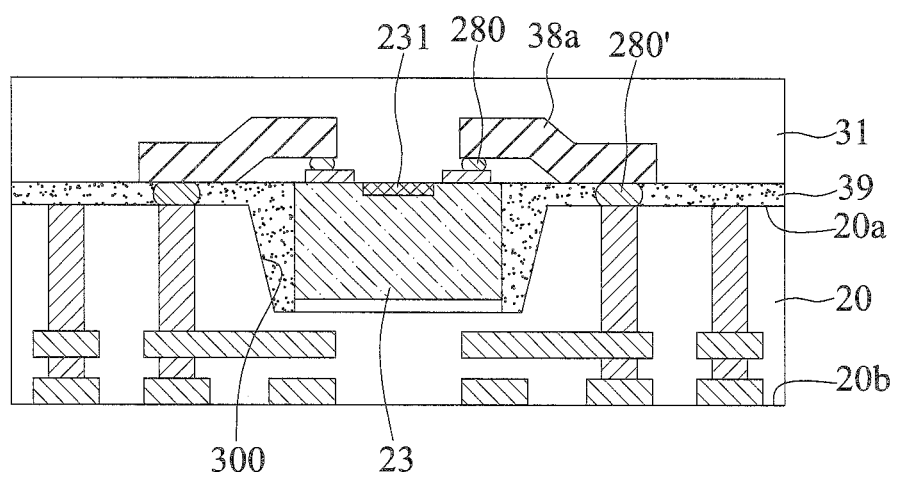
Figure 3A:
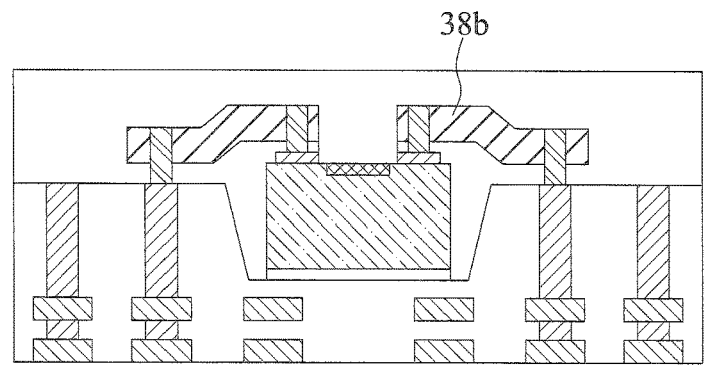
FIGS. 3A to 3C show other embodiments of the conductive structure of FIG. 3.
Figure 3B:
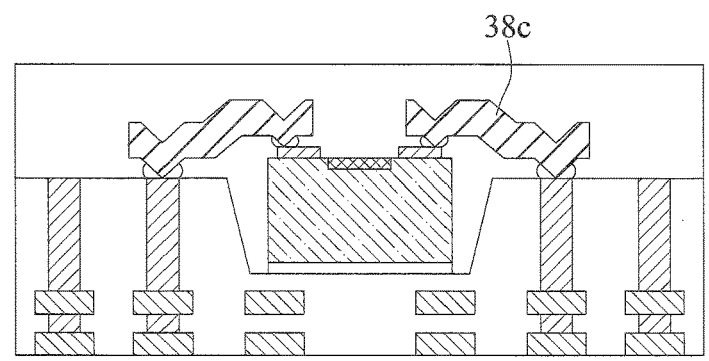
Figure 3C:
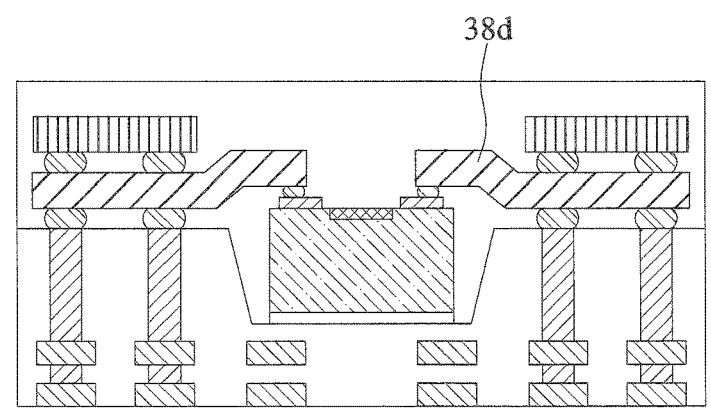
Figure 5:
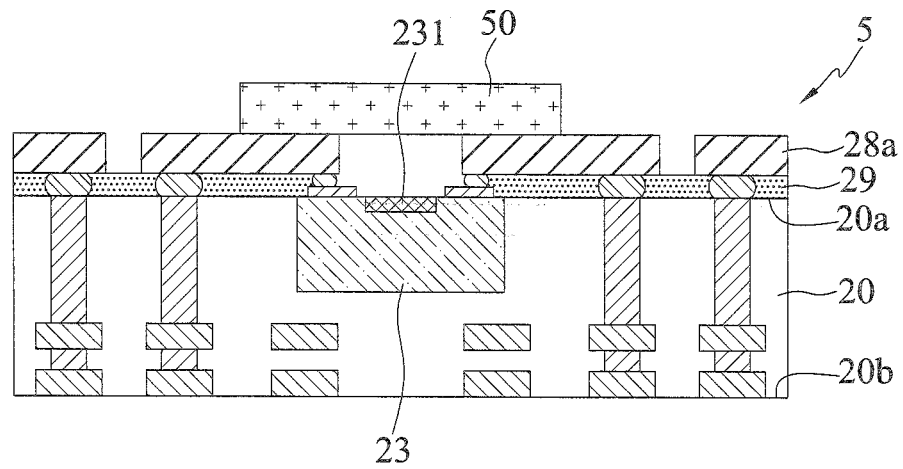
Figure 5:
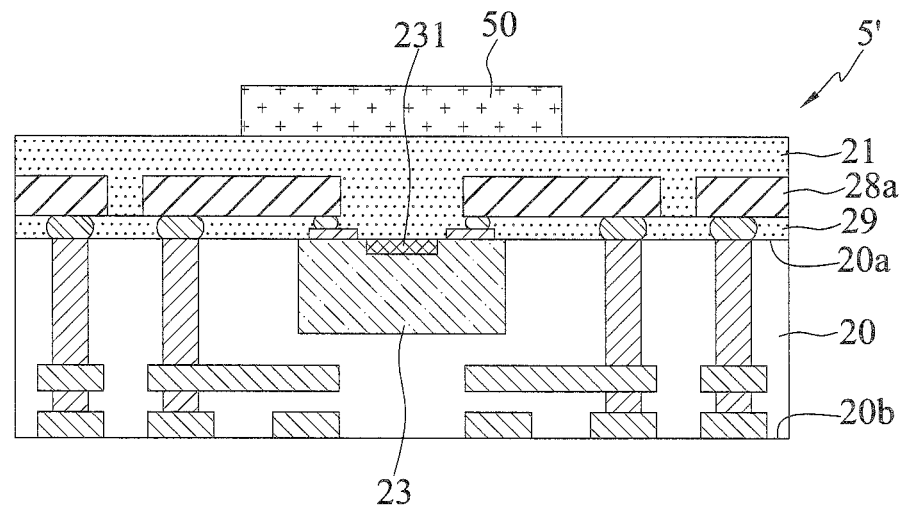

Further, the conductive structures of FIGS. 2B to 2D can be configured to have a plurality of height levels, thus forming conductive structures 38b to 38d of FIGS. 3A to 3C.

In an embodiment, the conductive structures 38a to 38d are made of pure metal or a combination of metal and an organic film.

In the electronic packages 3, 3', since the electronic element 23 is disposed in the recessed portion 300 of the insulator 20, the thickness of the overall structure is reduced.

FIGS. 4 to 4'' are schematic cross-sectional views of electronic packages 4, 4' according to a third embodiment of the present disclosure. The third embodiment differs from the second embodiment in the addition of a passive element 40.

Referring to FIGS. 4 and 4', the electronic packages 4, 4' further have another electronic element 40 bonded to the insulator 20.

The electronic element 40 is an active element such as a semiconductor chip, a passive element such as a resistor, a capacitor or an inductor, or a combination thereof. In the present embodiment, the electronic element 40 is a passive element.

The electronic element 40 is partially disposed in the insulator 20 and partially protrudes from the first surface 20a of the insulator 20. The electronic element 40 is electrically connected to the conductive posts 24.

Alternatively, the electronic element 40 is completely disposed in the insulator 20, as shown in FIG. 4', or completely disposed on the first surface 20a of the insulator 20, as shown in FIG. 4''.

In addition, referring to FIG. 4' or FIG. 4'', a covering layer 31 is further formed on the first surface 20a of the insulator 20 and covering the electronic elements 23, 40, the conductive structure 38a and the sensing area 231.

FIGS. 5 and 5' are schematic cross-sectional views of electronic packages 5, 5' according to a fourth embodiment of the present disclosure. The fourth embodiment differs from the above-described embodiments in that the electronic packages 5, 5' are applied in camera lenses. In particular, a transparent element 50 is added.

Referring to FIG. 5, the electronic package 5 further has a transparent element 50 such as a lens or glass that covers the sensing area 231 of the electronic element 23.

In the present embodiment, the electronic package 5 is similar to the structure of FIG. 2A and the transparent element 50 is disposed on the conductive structure 28a. As such, the present disclosure dispenses with the conventional support members so as to reduce the thickness of the overall structure.

Alternatively, referring to FIG. 5', the electronic package 5 is similar to the structure of FIG. 2A' and the transparent element 50 is disposed on the covering layer 21.

Further, in the above-described embodiments, the circuit layer 22 can be in contact with the inactive surface 23b of the electronic element 23 directly or through an adhesive layer to facilitate heat dissipation of the electronic element 23.

The present disclosure provides a conductive structure 6. As shown in FIGS. 2-5, the conductive structure 6 comprises a carrier 61, a plurality of lead frames 28 disposed on the carrier 61, and a plurality of conductive portions 60 disposed on the lead frames 28.

The carrier 61 is removed after the electronic packages 2a-2d, 2a'-2d', 3, 3', 4, 4', 5 and 5' are assembled, and is a tape, release film, prepreg, or a supporting sheet, such as polyimide (PI), polyethylene terephthalate (PET), epoxy, bismaleimide triazine (BT), FR4, FR5, and reinforced carbon-carbon (RCC).

The conductive portions 60 can be referred to as conductive bumps 280 and 280', the openings 281, or the protruding contacts 282.

The plurality of lead frames 28 are arranged in the shape of a ring, and form an opening area A that corresponds in position to the electronic element 23 when the electronic packages 2a-2d, 2a'-2d', 3, 3', 4, 4', 5 and 5' are assembled.

In the above-described electronic packages, the electronic element is embedded in the insulator to reduce the thickness of the overall structure.

Further, the conductive structure such as a lead frame is electrically connected to the electronic element. As such, the present disclosure does not need to consider the wire loop of bonding wires or the thickness of an encapsulant as in the prior art. Therefore, the thickness of the electronic packages is easy to control, thus achieving a greatly reduced thickness.

Furthermore, since the present disclosure uses a non-semiconductor process, the fabrication cost is reduced.

In addition, the electronic packages can be easily adjusted according to the practical need, thereby improving the design flexibility.

The above-described descriptions of the detailed embodiments are only to illustrate the preferred implementation according to the present disclosure, and it is not to limit the scope of the present disclosure. Accordingly, all modifications and variations completed by those with ordinary skill in the art should fall within the scope of present disclosure defined by the appended claims.

What is claimed is:

1. An electronic package, comprising:
   an insulator having opposite first and second surfaces;
   a circuit structure formed in the insulator and communicating with the first surface of the insulator, wherein the circuit structure has a plurality of circuit layers and a plurality of conductive posts electrically connecting the circuit layers, and the conductive posts communicate with the first surface of the insulator;
   an electronic element embedded in the first surface of the insulator and having a plurality of electrode pads and at least a sensing area exposed from the first surface of the insulator; and
   a conductive structure disposed on the first surface of the insulator and electrically connected to the plurality of electrode pads of the electronic element and the conductive posts of the circuit structure, wherein the conductive structure is a lead frame and the sensing area is exposed from the conductive structure, and the conductive structure is attached to the first surface of the insulator and electrically connected to the electronic element and the conductive posts through a plurality of first conductive elements.

2. The electronic package of claim 1, wherein the electronic element protrudes from the first surface of the insulator.

3. The electronic package of claim 1, wherein the conductive structure has a plurality of height levels.

4. The electronic package of claim 1, wherein the first conductive elements are conductive bumps.

5. The electronic package of claim 1, further comprising another electronic element, electrically connected to the conductive structure through a plurality of conductive bumps.

6. The electronic package of claim 1, wherein the lead frame has a plurality of openings and the plurality of first conductive elements are formed in the openings and electrically connected to the electronic element.

7. The electronic package of claim 1, wherein the conductive structure has a plurality of protruding contacts serving as the first plurality of conductive elements.

8. The electronic package of claim 1, further comprising a plurality of second conductive elements formed on the second surface of the insulator.

9. The electronic package of claim 1, further comprising a recessed portion formed on the first surface of the insulator, wherein the electronic element is received in the recessed portion.

10. The electronic package of claim 1, further comprising a covering layer covering the sensing area of the electronic element.

11. The electronic package of claim 1, wherein the conductive structure has a step shape.

12. The electronic package of claim 1, further comprising another electronic element bonded to the insulator.

13. The electronic package of claim 12, wherein the another electronic element is an active element, a passive element or a combination thereof.

14. The electronic package of claim 12, wherein the another electronic element is partially disposed in the insulator, and partially protrudes from the first surface of the insulator.

15. The electronic package of claim 14, wherein the conductive posts formed in the insulator are electrically connected to the another electronic element.

16. The electronic package of claim 12, wherein the another electronic element is completely disposed in the insulator.

17. The electronic package of claim 12, wherein the another electronic element is completely disposed on the first surface of the insulator.

18. The electronic package of claim 1, further comprising a transparent element covering the sensing area of the electronic element.

* * * * *